United States Patent [19]

Yamamoto et al.

[11] Patent Number: 5,104,844
[45] Date of Patent: Apr. 14, 1992

[54] PROCESS OF PREPARING CATALYSTS FOR PRODUCING METHACRYLIC ACID

[75] Inventors: Shinji Yamamoto; Yutaka Kinoshita; Motomu Oh-Kita, all of Otake, Japan

[73] Assignee: Mitsubishi Rayon Co., Ltd., Tokyo, Japan

[21] Appl. No.: 654,455

[22] Filed: Feb. 13, 1991

[30] Foreign Application Priority Data

Feb. 15, 1990 [JP] Japan ................................ 2-032585

[51] Int. Cl.$^5$ .................... B01J 21/06; B01J 21/10; B01J 23/02; B01J 23/04; B01J 23/06; B01J 23/22
[52] U.S. Cl. .................................. 502/200; 502/205; 502/209
[58] Field of Search .................. 502/209, 205, 200; 562/534, 535

[56] References Cited

U.S. PATENT DOCUMENTS

| | | |
|---|---|---|
| 3,998,876 | 12/1976 | Kato et al. |
| 4,000,088 | 12/1976 | Shimiza et al. |
| 4,001,316 | 1/1977 | Ishimi .............................. 502/209 X |
| 4,273,676 | 6/1981 | Matsumoto et al. ................ 502/209 |
| 4,419,270 | 12/1983 | Ueshima et al. .................... 502/209 |
| 4,467,113 | 8/1984 | Matsumoto et al. ............ 502/209 X |
| 4,530,916 | 7/1985 | Matsumoto et al. ................ 502/209 |
| 4,745,217 | 5/1988 | Matsumoto et al. ............ 502/209 X |

FOREIGN PATENT DOCUMENTS

| | | | |
|---|---|---|---|
| 0350862 | 1/1990 | European Pat. Off. ............ 562/535 |
| 2-022243 | 1/1990 | Japan . |

OTHER PUBLICATIONS

Kirk-Othmer, *Encyclopedia of Chemical Technology*, 3rd ed., John Wiley & Sons, New York, 1978, vol. 2, pp. 471 and 516–536.

Kirk-Othmer, *Concise Encyclopedia of Chemical Technology*, John Wiley & Sons, New York, 1985, p. 92.

*Primary Examiner*—W. J. Shine
*Assistant Examiner*—Douglas J. McGinty
*Attorney, Agent, or Firm*—Armstrong, Nikaido, Marmelstein, Kubovcik & Murray

[57] ABSTRACT

A process for preparing a multi-component catalyst for producing methacrylic acid containing phosphorus, molybdenum and vanadium comprising using in preparing the catalyst, at least one number selected from the group consisting of the oxide, carbonates, acetates and hydroxides of each catalyst-constituting element as a source of the element; dissolving or dispersing the selected sources of the catalyst-constituting elements in water; adding at least one member selected from the group consisting of ammonium carbonate, ammonium hydrogen-carbonate, ammonium sulfate and ammonium hydrogen-sulfate to the resulting aqueous solution or dispersion; removing water therefrom and then heat-treating the residual product.

5 Claims, No Drawings

PROCESS OF PREPARING CATALYSTS FOR PRODUCING METHACRYLIC ACID

BACKGROUND OF THE INVENTION

1. Field of the Invention

The present invention relates to a process for preparing a catalyst used in producing methacrylic acid by the gas-phase catalytic oxidation of methacrolein.

2. Description of the Prior Art

Hitherto, in producing methacrylic acid by the gas-phase catalytic oxidation of methacrolein, it is advantageous to keep the yield high at a low reaction temperature from standpoints such as the life of catalysts, inhibition of side reactions, cost of equipments, etc. However, when catalysts prepared by the conventional methods are used, satisfactory results are not always obtained.

One possible reason for this is that the specific surface area and distribution of micropores of the catalyst which are important to the oxidation reaction have not sufficiently been controlled. In order to improve these defects, the following various trials have been made at the time of preparation of the catalyst: Addition of carboxylic acids or polyhydric alcohols (refer to Japanese Patent Application Kokai No. 51-136615), addition of an alcohol and a glycol (refer to ibid. No. 55-73347), addition of a pyridine compound (refer to ibid. No. 47-38591, No. 57-171444), addition of a quinoline compound (refer to ibid. No. 60-209258), addition of ammonium ions (refer to ibid. No. 57-165040), etc. However, these methods have various defects, for example, reaction results are not satisfactory; catalytic activity largely lowers with the lapse of time; reaction temperature is too high; and the heat-treatment method which is a catalyst-activating treatment is troublesome because of organic substances being used. The catalysts thus obtained, therefore, are not always satisfactory as industrial catalysts.

Specifically, when organic substances such as quinoline compounds, pyridine compounds, carboxylic acids, etc. are used, there are defects that a burning phenomenon is easy to appear to result in the collapse of a catalyst structure when the catalyst after shaping is subjected to the heat treatment, and also that the distribution of micropores is difficult to control. When alcohols are added, the catalyst structure is easy to change and those giving satisfactory reaction results are difficult to obtain. When ammonia is added as an ammonium ion source, there is a defect of the catalyst structure being easy to change. Further, when ammonium nitrate is added as the ammonium ion source, there is a defect of catalyst-shaping machines and/or catalyst-drying equipments being injured because of its corrosive action.

SUMMARY OF THE INVENTION

An object of the present invention is to provide a novel process for preparing a catalyst for advantageously producing methacrylic acid from methacrolein.

In order to improve the conventional catalyst-preparation methods, the present inventors have studied with particular notice given to the physical properties of the catalyst, and as a result have found a novel process for preparing a catalyst which works effectively at lower reaction temperatures and yet gives methacrylic acid in higher yields than when catalysts prepared by the conventional methods are used.

The present invention relates to a process for preparing a multi-component catalyst for producing methacrylic acid containing phosphorus, molybdenum and vanadium comprising using in preparing the catalyst, at least one member selected from the group consisting of the oxides, carbonates, acetates and hydroxides of each catalyst-constituting element as a source of the element; dissolving or dispersing the selected sources of the catalyst-constituting elements in water; adding at least one member selected from the group consisting of ammonium carbonate, ammonium hydrogen-carbonate, ammonium sulfate and ammonium hydrogen-sulfate to the resulting aqueous solution or dispersion; removing water therefrom and then heat-treating the residual product.

DESCRIPTION OF PREFERRED EMBODIMENTS

As the catalyst obtained according to the present invention, a catalyst represented by the following formula is preferred:

$$P_a Mo_b V_c Cu_d X_e Y_f (NH_4)_g O_h$$

wherein P, Mo, V, Cu, NH$_4$ and O are phosphorus, molybdenum, vanadium, copper, ammonium group and oxygen, respectively, X is at least one element selected from the group consisting of potassium, rubidium, cesium and thallium, Y is at least one element selected from the group consisting of silver, magnesium, zinc, arsenic, germanium, silicon, tungsten, boron, bismuth, chromium, lanthanum, barium, antimony, iron, zirconium, tellurium and cerium, a, b, c, d, e, f and h are an atomic ratio of each element, g is the number of ammonium molecules, being 0.01 to 2, and when b is 12, a is 0.5 to 3, c is 0.01 to 3, d is 0.01 to 2, e is 0.01 to 2 and f is 0 to 5, and h is the number of oxygen atoms necessary to satisfy the valence of each component.

Materials for molybdenum used to prepare the catalyst include molybdenum trioxide and molybdic acid. Particularly, good results are obtained when molybdenum trioxide is used. Materials for other catalyst-constituting elements include the oxides, carbonates, acetates and/or hydroxides of said elements.

In practicing the present invention, for example, the following procedure is taken: The materials for molybdenum, vanadium and phosphorus are dissolved or dispersed in water, the resulting aqueous solution or dispersion is heated to carry out a reaction sufficiently and then other materials for the catalyst are added at the same time or successively. In the present invention, ammonium carbonate, ammonium hydrogen-carbonate, ammonium sulfate and/or ammonium hydrogen-sulfate may be added at the time of addition of other materials for the catalyst. Particularly, however, good results are obtained when ammonium carbonate, ammonium hydrogen-carbonate, ammonium sulfate and/or ammonium hydrogen-sulfate dissolved in water is added after all of other materials for the catalyst are added.

The amount of ammonium carbonate, ammonium hydrogen-carbonate, ammonium sulfate and/or ammonium hydrogen-sulfate is 1 to 50 wt.%, particularly preferably 3 to 30 wt.% based on the total weight of all the materials for the catalyst.

Next, water is removed from a mixture containing the materials for the catalyst and ammonium carbonate, ammonium hydrogen-carbonate, ammonium sulfate and/or ammonium hydrogen-sulfate, and on heat-treating the residual product, the desired catalyst is obtained. It is desirable to carry out the heat treatment, for example, at a temperature of 300° to 430° C. while streaming air and/or a gas containing 5 vol.% or more of oxygen.

The catalyst used in the present invention works effectively without a carrier, but it is preferred to use the catalyst supported on or diluted with an inert carrier such as silica, alumina, silica-alumina, silicon carbide, etc.

When methacrylic acid is produced with the catalyst obtained by the present invention, the methacrolein concentration of the gas used as a material can be changed in a wide range, but 1 to 20% by volume, particularly 3 to 10% by volume is preferably used. Methacrolein, a material, may contain small amounts of impurities such as water, a saturated lower aldehyde, etc. These impurities give substantially no effect to the reaction.

As an oxygen source, the use of air is economical, but air made rich in pure oxygen may be used if necessary. The oxygen concentration of the gas used as a material is determined by the molar ratio to methacrolein. The value of this molar ratio is 0.3 to 4, particularly preferably 0.4 to 2.5.

The gas, a material, may be diluted with an inert gas such as nitrogen, steam, carbon dioxide, etc. Reaction pressure is preferably atmospheric pressure to several atmospheres. Reaction temperature is 200° to 420° C., particularly preferably 230° to 400° C. The reaction can be carried out by using either a fixed bed or fluidized bed.

In the following examples and comparative examples, the conversion of methacrolein and the selectivity of methacrylic acid produced are defined as follows:

$$\text{Conversion of methacrolein (\%)} = \frac{\text{Number of moles of reacted methacrolein}}{\text{Number of moles of supplied methacrolein}} \times 100$$

$$\text{Selectivity of methacrylic acid (\%)} = \frac{\text{Number of moles of produced methacrylic acid}}{\text{Number of moles of reacted methacrolein}} \times 100$$

In the following examples and comparative examples, parts are weight, and analyses were carried out by gas chromatography.

EXAMPLE 1

100 Parts of molybdenum trioxide, 2.6 parts of vanadium pentoxide and 6.7 parts of 85% phosphoric acid were added to 800 parts of pure water, and the resulting mixture was heated under reflux for 6 hours. Thereafter, 1.2 parts of copper acetate was added, and refluxing was continued for further 3 hours with heating. After refluxing, 11.2 parts of cesium hydrogen-carbonate dissolved in 100 parts of pure water and then 5.6 parts of ammonium carbonate dissolved in 100 parts of pure water were added, and the resulting mixed solution was evaporated to dryness with heating. The solid product obtained was dried at 120° C. for 16 hours, shaped by applying pressure and heat-treated at 380° C. for 5 hours under air stream. The composition of components except oxygen of the resulting catalyst was $P_1Mo_{12}V_{0.5}Cu_{0.1}Cs_1(NH_4)_{0.3}$ (catalysts described herein-below also are represented by the composition of components except oxygen).

A reactor was filled with this catalyst, and a mixed gas consisting of 5 vol.% of methacrolein, 10 vol.% of oxygen, 30 vol.% of steam and 55 vol.% of nitrogen was passed through the reactor at a reaction temperature of 285° C. for a contact time of 3.6 seconds. The product was collected and analyzed by gas chromatography to find that the conversion of methacrolein was 84.1% and the selectivity of methacrylic acid was 83.8%.

COMPARATIVE EXAMPLE 1

A catalyst having the same composition as in Example 1 was prepared without adding ammonium carbonate. Using this catalyst, reaction was carried out under the same conditions as in Example 1 except that the reaction temperature was changed to 290° C. As a result, it was found that the conversion of methacrolein was 80.0% and the selectivity of methacrylic acid was 81.6%.

EXAMPLE 2

A catalyst having a composition, $P_1Mo_{12}V_{0.5}Cu_{0.1}K_1Si_{0.3}As_{0.2}(NH_4)_{0.2}$, was prepared according to Example 1 except that ammonium hydrogen-carbonate of 9.2 parts based on 100 parts of molybdenum trioxide was added in place of ammonium carbonate, and that potassium carbonate, silica sol and arsenic acid were used.

Using this catalyst, reaction was carried out under the same conditions as in Example 1 except that the reaction temperature was changed to 270° C. As a result, it was found that the conversion of methacrolein was 84.3% and the selectivity of methacrylic acid was 86.6%.

COMPARATIVE EXAMPLE 2

A catalyst having the same composition as in Example 2 was prepared without adding ammonium hydrogen-carbonate. Using this catalyst, reaction was carried out under the same conditions as in Example 1 except that the reaction temperature was changed to 280° C. As a result, it was found that the conversion of methacrolein was 78.9% and the selectivity of methacrylic acid was 84.2%.

EXAMPLE 3

A catalyst having a composition, $P_{1.5}Mo_{12}V_{0.8}Cu_{0.2}Rb_1Ce_{0.1}Fe_{0.2}Sb_{0.8}(NH_4)_{0.4}$, was prepared according to Example 1 except that a part of ammonium carbonate was replaced by ammonium sulfate and a mixed solution containing 2.8 parts of ammonium carbonate and 3.8 parts of ammonium sulfate based on 100 parts of molybdenum trioxide was added, and that rubidium acetate, cerium oxide and iron oxide were used. In this case, antimony trioxide was used as the source of antimony.

Using this catalyst, reaction was carried out under the same conditions as in Example 1 except that the reaction temperature was changed to 270° C. As a result, it was found that the conversion of methacrolein was 89.6% and the selectivity of methacrylic acid was 88.7%.

COMPARATIVE EXAMPLE 3

A catalyst having the same composition as in Example 3 was prepared without adding ammonium carbonate and ammonium sulfate. Using this catalyst, reaction was carried out under the same conditions as in Example 1 except that the reaction temperature was changed to 270° C. As a result, it was found that the conversion of methacrolein was 77.2% and the selectivity of methacrylic acid was 87.0%.

EXAMPLE 4

A catalyst having a composition, $P_{1.1}Mo_{12}V_{0.8}Cu_{0.2}K_{0.7}Cs_{0.3}Bi_{0.2}Sb_{0.7}(NH_4)_{0.4}$, was prepared according to Example 1 except that a part of ammonium carbonate was replaced by ammonium hydrogen-sulfate and a mixed solution containing 2.8 parts of ammonium carbonate and 11.5 parts of ammonium hydrogen-sulfate based on 100 parts of molybdenum trioxide was added, and that potassium carbonate, cesium hydrogen-carbonate and bismuth oxide were used. In this case, antimony pentoxide was used as the source of anitomony.

Using this catalyst, reaction was carried out under the same conditions as in Example 1 except that the reaction temperature was changed to 270° C. As a result, it was found that the conversion of methacrolein was 90.5% and the selectivity of methacrylic acid was 88.7%.

COMPARATIVE EXAMPLE 4

A catalyst having the same composition as in Example 4 was prepared without adding ammonium carbonate and ammonium hydrogen-sulfate. Using this catalyst, reaction was carried out under the same conditions as in Example 1 except that the reaction temperature was changed to 290° C. As a result, it was found that the conversion of methacrolein was 87.1% and the selectivity of methacrylic acid was 87.3%.

EXAMPLES 5 TO 7

Catalysts shown in Table 1 were prepared according to Example 1. Part in the table which represents the amount of an ammonium salt added means part by weight based on 100 parts by weight of molybdenum trioxide. Using these catalysts, reaction was carried out in the same manner as in Example 1 except that the reaction temperature was changed. The results also are shown in Table 1.

EXAMPLES 8 TO 10

Catalysts shown in Table 2 were prepared according to Example 3. Part in the table which represents the amount of an ammonium salt added means part by weight based on 100 parts by weight of molybdenum trioxide. Using these catalysts, reaction was carried out in the same manner as in Example 1 except that the reaction temperature was changed. The results also are shown in Table 2.

TABLE 2

| | Composition of catalyst | Amount of ammonium salt added (part) | Reaction temperature (°C.) | Conversion of methacrolein (%) | Selectivity of methacrylic acid (%) |
|---|---|---|---|---|---|
| Example 8 | $P_{1.2}Mo_{12}V_{0.6}Cu_{0.2}K_1Bi_{0.3}Sb_{0.3}Ba_{0.2}(NH_4)_{0.3}$ | Ammonium carbonate, 7 | 280 | 88.3 | 88.9 |
| Example 9 | $P_1Mo_{12}V_{0.5}Cu_{0.2}Cs_1Fe_{0.3}Sb_{0.6}La_{0.1}Ag_{0.05}(NH_4)_{0.5}$ | Ammonium sulfate, 10 | 280 | 89.1 | 88.1 |
| Example 10 | $P_1Mo_{12}V_{0.8}Cu_{0.1}Rb_1Zn_{0.2}Fe_{0.2}Sb_{0.7}W_{0.1}(NH_4)_{0.1}$ | Ammonium carbonate, 3 + ammonium sulfate, 7 | 280 | 90.1 | 88.8 |

What is claimed is:

1. A process for preparing a multi-component catalyst for producing methacrylic acid containing, as catalyst-constituting elements, phosphorus, molybdenum and vanadium, comprising using in preparing the catalyst, at least one member selected from the group consisting of the oxides, carbonate, acetates and hydroxides of each of said catalyst-constituting element as a source of the element, dissolving or dispersing selected sources of the catalyst-constituting elements in water; adding at least one member selected from the group consisting of ammonium carbonate, ammonium hydrogen carbonate, ammonium sulfate and ammonium hydrogen sulfate to the resulting aqueous solution or dispersion; removing water therefrom and then heat-treating the residual product.

2. A process according to claim 1, wherein said multi-component catalyst for producing methacrylic acid is one represented by the formula, $$P_aMo_bV_cCu_dX_eY_f(NH_4)_gO_h$$

wherein P, Mo, V, Cu, NH$_4$ and O are phosphorus, molybdenum, vanadium, copper, ammonium group and oxygen, respectively, X is at least one element selected from the group consisting of potassium, rubidium, cesium and thallium, Y is at least one element selected from the group consisting of silver, magnesium, zinc, arsenic, germanium, silicon, tungsten, boron, bismuth, chromium, lanthanum, barium, antimony, iron, zirconium, tellurium and cerium, a, b, c, d, e, f and h are an atomic ratio of each element, g is the number of ammo-

TABLE 1

| | Composition of catalyst | Amount of ammonium salt added (part) | Reaction temperature (°C.) | Conversion of methacrolein (%) | Selectivity of methacrylic acid (%) |
|---|---|---|---|---|---|
| Example 5 | $P_1Mo_{12}V_{0.5}Cu_{0.1}Tl_{0.8}Fe_{0.3}Zr_{0.1}Cr_{0.2}(NH_4)_{0.3}$ | Ammonium sulfate, 10 | 280 | 88.8 | 86.7 |
| Example 6 | $P_{1.1}Mo_{12}V_{0.5}Cu_{0.1}K_{0.8}Cs_{0.3}Fe_{0.3}Mg_{0.2}Te_{0.2}(NH_4)_{0.2}$ | Ammonium hydrogen + carbonate, 8 | 280 | 89.0 | 87.1 |
| Example 7 | $P_{1.2}Mo_{12}V_{0.8}Cu_{0.1}K_1Fe_{0.2}Ge_{0.2}B_{0.3}(NH_4)_{0.2}$ | Ammonium carbonate, 8 | 275 | 89.5 | 87.7 | nium molecules, being 0.01 to 2, and when b is 12, a is 0.5 to 3, c is 0.01 to 3, d is 0.01 to 2, e is 0.01 to 2 and f is 0 to 5, and h is the number of oxygen atoms necessary to satisfy the valence of each component.

3. A process according to claim 1, wherein the amount of ammonium carbonate, ammonium hydrogencarbonate, ammonium sulfate and ammonium hydrogen-sulfate is 1 to 50 wt.% based on the total weight of the materials for the catalyst.

4. A process as claimed in claim 1 wherein said heat treatment is at a temperature of about 300 to 430° C. in a gas comprising at least about 5 volume percent oxygen.

5. The product of the process of claim 1.

* * * * *